United States Patent

Yoshikawa et al.

[11] Patent Number: 5,637,399
[45] Date of Patent: Jun. 10, 1997

[54] SYNTHETIC RESIN NEEDLE

[75] Inventors: Makoto Yoshikawa, Kofu; Koichi Tachikawa; Masaaki Kasai, both of Yamanashi, all of Japan

[73] Assignee: Terumo Kabushiki Kaisha, Tokyo, Japan

[21] Appl. No.: 736,912

[22] Filed: Oct. 25, 1996

Related U.S. Application Data

[63] Continuation of Ser. No. 404,585, Mar. 15, 1995, abandoned.

[30] Foreign Application Priority Data

Mar. 17, 1994 [JP] Japan .................. 6-047448

[51] Int. Cl.$^6$ .................................. A61M 5/32
[52] U.S. Cl. .................. 428/369; 428/376; 604/272
[58] Field of Search ................. 428/369, 376; 604/272

[56] References Cited

U.S. PATENT DOCUMENTS

| | | | |
|---|---|---|---|
| 2,512,568 | 6/1950 | Saffir | 604/272 |
| 3,715,254 | 2/1973 | Tolgyesi | 428/376 |
| 4,646,618 | 3/1987 | Kurth | 89/1.816 |
| 4,792,481 | 12/1988 | O'Connor | 428/375 |
| 4,838,877 | 6/1989 | Massau | 604/272 |
| 4,897,286 | 1/1990 | Kosuda | 427/44 |
| 5,250,756 | 10/1993 | Swift | 174/119 R |
| 5,324,563 | 6/1994 | Rogers | 428/375 |
| 5,350,221 | 9/1994 | Pearce | 301/104 |
| 5,380,580 | 1/1995 | Rogers | 428/219 |
| 5,458,614 | 10/1995 | Humphrey | 604/272 |

FOREIGN PATENT DOCUMENTS

| | | |
|---|---|---|
| 0174011 | 3/1986 | European Pat. Off. |
| 0566359 | 10/1993 | European Pat. Off. |

*Primary Examiner*—D. R. Wilson
*Attorney, Agent, or Firm*—Burns, Doane, Swecker & Mathis, LLP

[57] ABSTRACT

A synthetic resin needle of reinforced with combustible fibers whose longitudinal directions are arrayed straight or curvilinearly along the axial length of the needle. The reinforcing fibers may be dispersed uniformly in the synthetic resin of the needle, or in such a non-uniform manner that the concentration of the fibers in some portion around the peripheral wall of the needle is so scarce that the inner passage of the needle can be observed from outside.

12 Claims, 1 Drawing Sheet

SYNTHETIC RESIN NEEDLE

This application is a continuation of application Ser. No. 08/404,585, filed Mar. 15, 1995 now abandoned.

BACKGROUND OF THE INVENTION

1. Field of the Invention

This invention relates to a novel synthetic resin (plastic) needle having a high stiffness and toughness. In particular, it relates to a medical plastic needle, such as an intra-venous needle, an intra-venous catheter, a blood sampling needle or a needle of administration set.

2. Description of Background Art

A metal such as stainless steel is generally employed as a material for an intra-venous needle. An intra-venous needle made of a metal is certainly advantageous in that the wall thickness of the needle can be made very thin so that a large flow rate can be secured even if the diameter of the needle is rather small and the needle edge can be sharply abraded so that smooth piercing by the needle can be achieved. However, since an intra-venous needle made of a metal can not be discarded as combustible waste after use, it is disposed of after use in its original form. Accordingly, the development of a combustible intra-venous needle would be highly desirable. In order to meet this, we have studied the use of synthetic resins for an intra-venous or other needle.

When an intra-venous needle is solely composed of a synthetic resin however, it is difficult to obtain sufficient stiffness and strength to avoid deformation or breakage of the edge of the synthetic resin needle, which detract from the capacity of the needle to penetrate easily. On the other hand, when a filler is added to the synthetic resin needle with a view to improving the stiffness of the needle, the toughness of the needle may instead be lowered though the stiffness of the needle may be improved, thereby increasing on the contrary the possibility of the needle being broken during penetration.

Accordingly, the problem faced is to develop a synthetic resin needle having a sufficient stiffness and at the same time a sufficient toughness to withstand actual usage as, e.g., an intra-venous needle and at the same time being capable of being disposed as combustible waste after use.

SUMMARY OF THE INVENTION

According to the present invention, the following five measures (1) to (5) are taken for solving the above problems.

(1) A synthetic resin needle is reinforced with combustible fibers whose longitudinal directions are arrayed (straight or curvilinearly) along the axial length of the needle;

(2) The reinforcing fibers are respectively arrayed along the full length of the needle;

(3) The reinforcing fibers are uniformly dispersed in the synthetic resin of the needle;

(4) The reinforcing fibers may be introduced into the wall of the needle in such a non-uniform manner that most of the reinforcing fibers are located near the peripheral surface of the needle; or (5) The needle may be solid or hollow tube; when it is a hollow tube, the reinforcing fibers may be introduced into the wall of the needle in such a non-uniform manner that the concentration of the fibers in some portion around the peripheral wall of the needle is so scarce that the inner passage of the needle can be observed from outside.

The basic structure of synthetic resin needle of this invention is formed of a fiber-reinforced resin, and is characterized in that it is combustible, the fibers used for the reinforcing being combustible and oriented from one end of the needle toward the other end.

DESCRIPTION OF THE PREFERRED EMBODIMENTS

Figure 1:
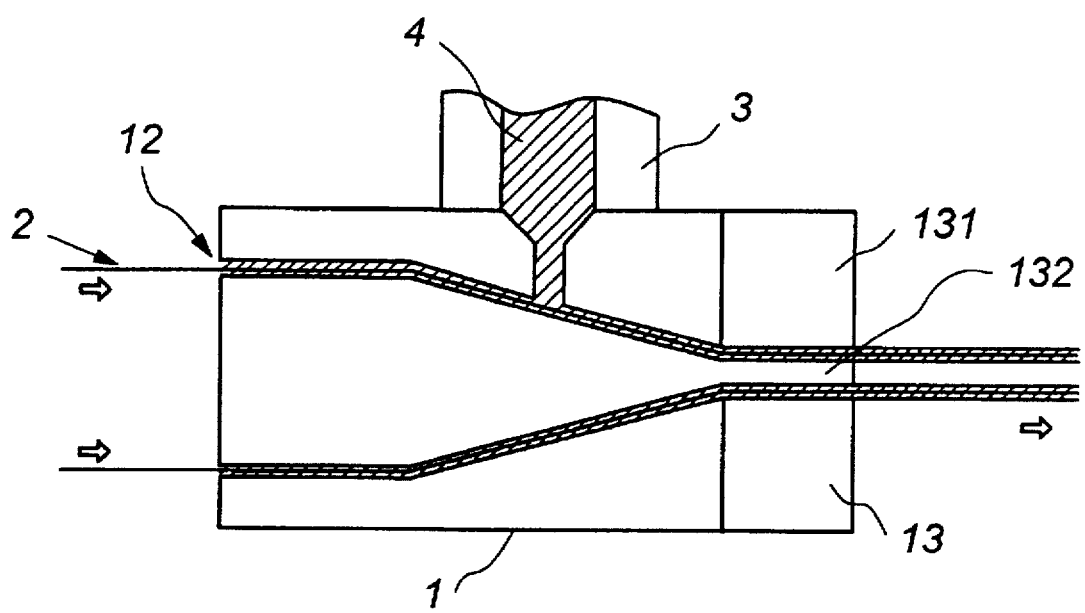
FIG. 1 is a sectional view of part of a molding machine used in a method of manufacturing a synthetic resin needle embodying this invention.

Examples of synthetic resin useful for the synthetic resin needle of this invention are cyclic olefinic resin, polyphenylene sulfide, polyether etherketone, polybutylene terephthalate, polycarbonate, polyamide, polyacetal, modified polyphenylene ether, polyester resin, polytetrafluoroethylene, fluorine plastic, polysulfone, polyether imide, polyether sulfone, polyether ketone, polyether lactone, crystalline polyester, polyamide imide, polyimide, or a thermosetting resin such as epoxy resin, unsaturated polyester resin, phenol resin, urea resin, melamine resin and polyurethane resin. Among these resins, thermoplastic resins are more preferable in view of easy handling and biological safety. It is further preferable to employ a thermoplastic resin of high elasticity having a flexural modulus of $2 \times 10^4$ Kg/cm$^2$ or more, for example polycarbonate, cyclic olefinic resin, polybutylene terephthalate, polyether etherketone, polyether imide, polyphenylene sulfide and crystalline polyether.

Fibers useful for reinforcing the synthetic resin needle of this invention are those which are combustible. The term 'combustible' or 'disposable by combustion' used herein should be understood to include a substance being deformed to substantially lose its original shape e.g. by fusion ignition or decomposition as a result of heating it in an incinerator or garbage furnace. Specific examples of such combustible fibers are carbon fiber, graphite fiber, aramid fiber, polyethylene fiber, polyvinylalcohol fiber, aromatic polyester fiber, polyimide fiber, polyamide imide fiber, heterocyclic high performance fiber, polyamide fiber, polyacetal fiber, glass fiber and polyarylate fiber. Among these combustible fibers, those having an elastic modulus of $5.0 \times 10^3$ Kg/mm$^2$ or more, such as carbon fiber, aramid fiber, heterocyclic high performance fiber, polyarylate fiber and glass fiber are preferably used in view of attaining a sufficient stiffness. More preferably, those having an elastic modulus of $10.0 \times 10^3$ Kg/mm$^2$ or more, such as carbon fiber, aramid fiber and heterocyclic high performance fiber can be used. As for the thickness of the fiber, those having a length of 1 to 50 μm, preferably 5 to 25 μm can be used.

The amount of the fiber to be added to the resin material constituting the main body of the synthetic resin needle of this invention depends on the kinds of synthetic resin or on the combination of fibers, but usually ranges from about 10 to 80% by volume, preferably 30 to 80% by volume, more preferably 40 to 70% by volume.

When a synthetic resin having high transparency such as polycarbonate is used for the manufacture of a hollow needle, and long reinforcing fibers are introduced into the resin in such a manner that the fibers are spaced apart in the annular section of the needle, it is possible to observe a liquid running through the inner passage of the needle with the naked eye.

The elastic modulus of synthetic resin needle thus obtained should preferably be $20 \times 10^4$ Kg/cm$^2$ or more, more preferably $30 \times 10^4$ Kg/cm$^2$ or more, most preferably $50 \times 10^4$ Kg/cm$^2$ or more.

A method of manufacturing a synthetic resin needle of this invention will be explained with reference to a hollow needle.

Referring to FIG. 1, elongated fibers 2 are continuously introduced into a fiber-inserting port 12 formed at the rear end of a crosshead 1 connected to an extruder machine (not shown). The fibers thus introduced from the fiber-inserting port 12 are then advanced toward the extruding portion 13. On the other hand, a thermoplastic resin heated and melted in the extruder is also introduced into the crosshead 1 to be impregnated into the fibers 2 advanced to this extruding portion 13. The fibers thus impregnated with the resin are drawn out of the space between the die 131 and mandrel 132 at a speed adjusted in conformity with the extruding speed of the resin thereby obtaining a tubular body. The tubular body thus extruded is then cooled and solidified obtaining a hollow needle.

With this machine, a cylindrical or tubular body can be extruded from a synthetic resin and reinforcing long fibers. The dimension of the tubular body should be 0.5 mm to 5.0 mm in outer diameter, and may be solid or if hollow have a wall thickness of down to 0.2 mm. The tubular body may be manufactured by forming it continuously with the extruder as explained above, discontinuously with an injection molding machine to obtain a discrete length of tubular body. The tubular body thus obtained is then cut to a desired length and sharpened to form a cutting edge thereby obtaining a synthetic resin needle. Any desired method of sharpening the tubular body for forming a cutting edge can be employed, for example introducing the tubular body into a heated mold, grinding the tubular body with a grindstone, or cutting the tubular body with laser, water jet or an edged tool. The shape of cutting edge of needle may be an open end of Lancet type, or a cone shape having a side opening communicating with the inner passage of the needle and opening outward. The synthetic resin needle thus obtained can be fixed by means of an adhesive, fusion-bonding or high frequency bonding to a hub provided with a connecting part to be mounted on a syringe.

When the molding of the needle is carried out by uniformly dispersing the fibers 2 in the fiber-inserting port 12 and the crosshead portion 1, a synthetic resin needle having the fibers 2 dispersed substantially uniformly throughout the needle can be obtained. Whereas, when the molding of the needle is carried out by disposing most of the fibers 2 near the peripheral portion of the inner passage of the crosshead, a synthetic resin needle is obtained having the fibers 2 non-uniformly dispersed in the needle, i.e. the fibers 2 are concentrated near the peripheral surface of the needle.

It is also possible to incorporate fillers or short fibers into the resin for improving the stiffness of the needle. Examples of short fibers useful in this invention are whisker, inorganic fillers (such as silica and talc), glass fiber, carbon fiber, graphite fiber and aramid fiber. Examples of whisker are titanium oxide, aluminum borate, potassium titanate and graphite. The amount of the short fibers may desirably be up to 30% by volume based on the total volume of a synthetic resin needle. The dimension of the short fiber should desirably be 0.01 to 50 µm, more preferably 0.05 to 10 µm in diameter, 1.0 to 100 µm, more preferably 3 to 50 µm in length.

EXAMPLE 1

A bundle of long fibers consisting of 7800 carbon fibers (7 µm in diameter, BESFIGHT HTA, Toyo Rayon Co., Ltd., elastic modulus: $24 \times 10^4$ Kg/mm$^2$), which is equivalent to 30% by volume based on the total volume of the final molded body was continuously introduced, uniformly dispersed, into a fiber-inserting port formed at the rear end of a crosshead connected to an extruder machine. The carbon fibers thus introduced from the fiber-inserting port was then advanced toward the extruding portion. Polycarbonate (NOVALEX 7020, Mitsubishi Engineering Plastic Co., Ltd., elastic modulus: $2.3 \times 10^4$ Kg/cm$^2$) heated and melted in the extruder was also introduced into the crosshead whereby being impregnated into the carbon fibers advanced to this extruding portion. The carbon fibers thus impregnated with the resin were drawn out of the space between the die and mandrel thereby extruding a tubular body of polycarbonate in which the carbon fibers were uniformly dispersed. The tubular body thus extruded was then cooled and solidified obtaining a pipe-shaped molded body having an inner diameter of 1.0 mm and an outer diameter of 1.5 mm.

The pipe-shaped molded body obtained was then cut into pieces, each having a length of 50 mm, which was then sharpened to form a cutting edge thereby obtaining a synthetic resin needle.

EXAMPLE 2

A bundle of long fibers consisting of 12,000 carbon fibers of the same kind as used in Example 1, which was equivalent to 45% by volume based on the total volume of molded body, was continuously introduced, uniformly dispersed, into the port, and then the same processes as used in Example 1 were repeated thereby obtaining a synthetic resin needle.

EXAMPLE 3

The same processes as conducted in Example 1 were repeated except that a bundle of long fibers consisting of 3,900 aramid fibers (12 µm in thickness, TWARON HM1056, Nihon Aramid Co., Ltd., elastic modulus: $13 \times 10^4$ Kg/mm$^2$), which was equivalent to 45% by volume based on the total volume of molded body, was employed in place of carbon fibers and continuously introduced, while being uniformly dispersed, into the crosshead, thereby obtaining as a final product a synthetic resin needle.

EXAMPLE 4

The processes of Example 2 were repeated using the carbon fibers except that titanium oxide whisker (1.0 µm in diameter, 5.0 µm in length, FTL-200, Ishihara Sangyo Co., Ltd.) in an amount of 9% by volume based on the total volume of molded body was continuously introduced together with the polycarbonate, uniformly dispersed, into the crosshead, thereby obtaining as a final product a synthetic resin needle.

EXAMPLE 5

A bundle of long fibers consisting of 15,000 carbon fibers of the same kind as used in Example 1, which was equivalent to 60% by volume based on the total volume of molded body was continuously introduced, uniformly dispersed, into the port, and then the same processes as used in Example 1 were repeated thereby obtaining as a final product a synthetic resin needle.

EXAMPLE 6

A bundle of long fibers consisting of 5,200 aramid fibers of the same kind as used in Example 3, which was equivalent to 60% by volume based on the total volume of molded body was continuously introduced, uniformly dispersed, into the port, and then the same processes as used in Example 3 were repeated thereby obtaining as a final product a synthetic resin needle.

EXAMPLE 7

The same processes as conducted in Example 1 were repeated except that a bundle of long fibers consisting of 1,400 polyacrylate fibers (23 μm in diameter, Vectran HT, KURARE Co., Ltd., elastic modulus: $8 \times 10^4$ Kg/mm$^2$), which was equivalent to 60% by volume based on the total volume of molded body, was employed in place of carbon fibers and continuously introduced, uniformly dispersed, into the port, thereby obtaining as a final product a synthetic resin needle.

EXAMPLE 8

The same processes as conducted in Example 1 were repeated except that a bundle of long fibers consisting of 15,000 carbon fibers of the same kind as used in Example 1, which was equivalent to 60% by volume based on the total volume of molded body, was continuously introduced, uniformly dispersed, into the port, and that the polycarbonate was replaced by cyclic olefin copolymer (APL 6015, Mitsui Petrochemical Co., Ltd., elastic modulus: $3.2 \times 10^4$ Kg/cm$^2$), which was heated and melted in an extruder and then introduced into the crosshead, thereby obtaining as a final product a synthetic resin needle.

EXAMPLE 9

The same processes as conducted in Example 1 were repeated except that a bundle of long fibers consisting of 15,000 carbon fibers of the same kind as used in Example 1, which was equivalent to 60% by volume based on the total volume of molded body, was continuously introduced, uniformly dispersed, into the port, and that the polycarbonate was replaced by polybutylene terephthalate (NOVADUR 5050, Mitsubishi Engineering Plastic Co., Ltd., elastic modulus: $2.4 \times 10^4$ Kg/cm$^2$), which was heated and melted in an extruder and then introduced into the crosshead, thereby obtaining as a final product a synthetic resin needle.

EXAMPLE 10

The same processes as conducted in Example 1 were repeated except that a bundle of long fibers consisting of 15,000 carbon fibers of the same kind as used in Example 1, which was equivalent to 60% by volume based on the total volume of molded body, was continuously introduced, uniformly dispersed, into the port, and that the polycarbonate was replaced by polyphenylene sulfide (TOHPLEN PPS T4, Tohnen Kagaku Co., Ltd., elastic modulus: $3.8 \times 10^4$ Kg/cm$^2$), which was heated and melted in an extruder and then introduced into the crosshead, thereby obtaining as a final product a synthetic resin needle.

EXAMPLE 11

The same processes as conducted in Example 1 were repeated except that a bundle of long fibers consisting of 15,000 carbon fibers of the same kind as used in Example 1, which was equivalent to 60% by volume based on the total volume of molded body, was continuously introduced, uniformly dispersed, into the port, and that the polycarbonate was replaced by polyether etherketone (Sumitomo Chemical Co., Ltd., VICTREX 450G elastic modulus: $3.8 \times 10^4$ Kg/cm$^2$), which was heated and melted in an extruder and then introduced into the crosshead, thereby obtaining as a final product a synthetic resin needle.

EXAMPLE 12

The same processes as conducted in Example 1 were repeated except that a bundle of long fibers consisting of 15,000 carbon fibers of the same kind as used in Example 1, which was equivalent to 60% by volume based on the total volume of molded body, was continuously introduced, uniformly dispersed, into the port, and that the polycarbonate was replaced by polyether imide (Japan GE Plastics Co., Ltd., Ultem 1000, elastic modulus: $3.4 \times 10^4$ Kg/cm$^2$), which was heated and melted in an extruder and then introduced into the crosshead, thereby obtaining as a final product a synthetic resin needle.

EXAMPLE 13

The same processes as conducted in Example 1 were repeated except that a bundle of long fibers consisting of 15,000 carbon fibers of the same kind as used in Example 1, which was equivalent to 60% by volume based on the total volume of molded body, was continuously introduced, uniformly dispersed, into the port, and that the polycarbonate was replaced by crystalline polyester (NOVACCURATE E310, Mitsubishe Engineering Plastic Co., Ltd., elastic modulus: $12 \times 10^4$ Kg/cm$^2$), which was heated and melted in an extruder and then introduced into the crosshead, thereby obtaining as a final product a synthetic resin needle.

EXAMPLE 14

A bundle of long fibers consisting of 18,000 carbon fibers of the same kind as used in Example 1, which was equivalent to 70% by volume based on the total volume of molded body, was continuously introduced, uniformly dispersed, into the crosshead, and then the same processes as used in Example 1 were repeated thereby obtaining as a final product a synthetic resin needle.

EXAMPLE 15

A bundle of long fibers consisting of 21,500 carbon fibers of the same kind as used in Example 1, which was equivalent to 80% by volume based on the total volume of molded body, was continuously introduced, uniformly dispersed, into the port, and then the same processes as used in Example 1 were repeated thereby obtaining as a final product a synthetic resin needle.

EXAMPLE 16

The processes of Example 1 were repeated except that 7,800 carbon fibers of the same kind as used in Example 1 were employed, and that the carbon fibers were introduced into the fiber-inserting port of the crosshead in such a non-uniform manner that carbon fibers were predominantly disposed at three peripheral portions of the passage within the crosshead thereby obtaining as a final product a synthetic resin needle.

EXAMPLE 17

The same processes as conducted in Example 1 were repeated except that a bundle of long fibers consisting of 2,600 carbon fibers of the same kind as used in Example 1, which was equivalent to 10% by volume based on the total volume of molded body, was continuously introduced, uniformly dispersed, into the port, and that polycarbonate was introduced into the crosshead together with 9% by volume of titanium oxide whisker (1.0 µm in diameter, 5.0 µm in length, FTL-200, Ishihara Sangyo Co., Ltd.) based on the total volume of molded body, thereby obtaining as a final product a synthetic resin needle.

Comparative Example 1

The processes of Example 1 were repeated except that carbon fibers were not used at all, thereby obtaining a synthetic resin needle.

Comparative Example 2

The processes of Example 1 were repeated except that carbon fibers were not used at all, and 19% by volume of short carbon fibers (each, 7 µm in diameter, 500 µm in length) based on the total volume of the molded body were added, thereby obtaining as a final product a synthetic resin needle.

Comparative Example 3

The processes of Example 1 were repeated except that carbon fibers were not used at all, and that the polycarbonate was replaced by polyphenylene sulfide (TOHPLEN PPS T4, Tothen Kagaku Co., Ltd., elastic modulus: $3.8 \times 10^4$ Kg/cm$^2$), and 19% by volume of short carbon fibers (each, 7 µm in diameter, 500 µm in length) based on the total volume of the molded body were added as a filler to the polyphenylene sulfide, the resultant mixture being heated and melted in an extruder and then introduced into the crosshead, thereby obtaining as a final product a synthetic resin needle.

Comparative Example 4

A bundle of long fibers consisting of 23,000 carbon fibers of the same kind as used in Example 1, which was equivalent to 90% by volume based on the total volume of molded body, was continuously introduced, uniformly dispersed, into the port, and then the same processes as used in Example 1 were repeated thereby obtaining as a final product a synthetic resin needle.

Test Example

The flexural modulus and modulus in bending of the synthetic needles obtained in the above Examples 1 to 17 and Comparative Examples 1 to 5 were measured in accordance with the test method stipulated in JIS K 7203. Additionally, the piercing performance of each of the synthetic needles obtained in the above Examples 1 to 17 and Comparative Examples 1 to 5 were measured by using as a piercing object an isoprene rubber stopper (JIS A hardness: 40, thickness: 6 mm) for an infusing bag (Terumo Co., Ltd., trade name: TERUPACK). The piercing performance was evaluated by driving the synthetic resin needle into the isoprene rubber stopper using 20 samples of each of the synthetic needles. The evaluation of the piercing performance was classified into 5 stages as explained below.

A: All of 20 needles could penetrate into the rubber stopper using an ordinary human strength.

B: Only 15 to 19 needles could penetrate into the rubber stopper due to the buckling or bending of edged tip portion of the needle.

C: Only 10 to 14 needles could penetrate into the rubber stopper due to the buckling or bending of edged tip portion of the needle.

D: Only 0 to 9 needles could penetrate into the rubber stopper due to the buckling or bending of edged tip portion of the needle.

The evaluated results of the piercing performance of the synthetic resin needles are shown in Table 1 together with the measured results of flexural modulus and modulus in bending.

TABLE 1

| Ex. No. | Flexural modulus ($10^4$Kg/cm$^2$) | Modulus in bending ($10^3$Kg/cm$^2$) | piercing performance |
|---|---|---|---|
| Ex. 1 | 25 | 3 | B |
| Ex. 2 | 35 | 5 | A |
| Ex. 3 | 25 | 3 | B |
| Ex. 4 | 55 | 8 | A |
| Ex. 5 | 54 | 7 | A |
| Ex. 6 | 35 | 4 | B |
| Ex. 7 | 28 | 3 | B |
| Ex. 8 | 52 | 7 | A |
| Ex. 9 | 50 | 6 | A |
| Ex. 10 | 55 | 8 | A |
| Ex. 11 | 55 | 9 | A |
| Ex. 12 | 54 | 9 | A |
| Ex. 13 | 55 | 6 | A |
| Ex. 14 | 55 | 6 | A |
| Ex. 15 | 45 | 4 | B |
| Ex. 16 | 22 | 3 | B |
| Ex. 17 | 20 | 3 | B |
| Com. Ex. 1 | 2 | 1 | D |
| Com. Ex. 2 | 15 | 2 | D |
| Com. Ex. 3 | 20 | 2 | C |
| Com. Ex. 4 | 10 | 2 | D |

When the elution test was conducted for the synthetic resin needles of the above Examples 1 to 17 in accordance with the Standard for Medical Intra-venous needle (Notice No. 443 from the Japanese Ministry of Health and Welfare, Dec. 20, 1970), every synthetic resin needle was found to meet the standard without difficulty.

Further, it was confirmed that the synthetic resin embodying this invention is fully applicable to various types of needle e.g. a needle of an administration set for effecting a connection with an infusion vessel, a blood sampling needle for taking blood from a living body, an intra-venous needle for infusing a medical liquid into a living body, or an indwelling needle. It was also confirmed that the synthetic resin needle embodying this invention could be fixed to a hub by means of an adhesive, fusion-bonding or high frequency bonding.

As explained above, since the fiber employed in the fiber-reinforced synthetic resin needle of this invention is combustible, the synthetic resin needle of this invention can be disposed of through burning. Further, the synthetic resin needle of this invention is free from rusting, and excellent in stiffness and toughness. When the fibers employed are adhesive to the synthetic resin constituting the main body of the needle, the sharpening of the edge of needle can be easily carried out. Since the fibers are continuously arrayed along the full length of the needle (straight or curvilinearly), the needle obtained is highly resistive to the bending load applied perpendicular to the longitudinal directions of the needle thereby making the needle more difficult to break as compared with a conventional synthetic resin needle containing only short fibers as a filler. Since the inclusion of long fibers in the synthetic resin needle would not cause the needle to become less tough or become fragile, it is possible to obtain a synthetic resin needle of excellent stiffness and toughness compared to a conventional synthetic resin needle containing only short fibers as a filler.

We claim:

1. A fiber-reinforced medical resin needle suitable for in vivo usage having an outer diameter ranging from 0.5 mm to 5.0 mm which is disposable by combustion and which contains from 30 to 80% by volume, based on the total weight of said resin needle, of continuous fibers which are oriented from one end of the needle toward the other end, said fibers being combustible and having a diameter ranging from 1 to 50 μm and an elastic modulus of at least $5.0 \times 10^3$ kg/m², and wherein said fiber-reinforced medical resin needle comprises a sharpened distal end and has attached thereto a hub which is attached to the proximal end portion of the medical resin needle.

2. The fiber-reinforced resin needle according to claim 1, wherein said fibers extend rectilinearly from one end to the other end of the needle.

3. The fiber-reinforced resin needle according to claim 1, wherein said fibers are selected from the group consisting of carbon fiber, graphite fiber, aramid fiber, polyethylene fiber, polyvinylalcohol fiber, aromatic polyester fiber, polyimide fiber, polyamide imide fiber, polyamide fiber, polyacetal fiber and polyarylate fiber.

4. The fiber-reinforced resin needle according to claim 1, wherein said fibers are selected from the group consisting of carbon fiber, aramid fiber and polyarylate fiber.

5. The fiber-reinforced resin needle according to claim 3, wherein said fibers are selected from the group consisting of carbon fiber and aramid fiber.

6. The fiber-reinforced resin needle according to claim 1, wherein said resin constituting said resin needle is selected from the group consisting of cyclic olefinic resin, polyphenylene sulfide, polyether etherketone, polybutylene terephthalate, polycarbonate, polyamide, polyacetal, modified polyphenylene ether, polyester resin, polytetrafluoroethylene, fluorine plastic, polysulfone, polyester imide, polyether sulfone, polyether ketone, polyether lactone, crystalline polyester, polyamide imide, polyimide, and thermosetting resins such as epoxy resin, unsaturated polyester resin, phenol resin, urea resin, melamine resin and polyurethane resin.

7. The fiber-reinforced resin needle according to claim 1, wherein said resin constituting said resin needle is selected from the group consisting of polycarbonate, cyclic olefinic resin, polybutylene terephthalate, polyether etherketone, polyeter imide, polyphenylene sulfide and crystalline polyester.

8. The fiber-reinforced resin needle according to claim 1, wherein said resin constituting said resin needle has a flexural modulus of $2 \times 10^4$ Kg/cm² or more.

9. The fiber-reinforced resin needle according to claim 1, wherein said fiber-reinforced resin needle has an elastic modulus of $20 \times 10^4$ Kg/cm² or more.

10. The fiber-reinforced resin needle according to claim 1, wherein said oriented fibers are non-uniformly dispersed in the synthetic resin of the needle.

11. The fiber-reinforced resin needle according to claim 1, wherein said fibers are non-uniformly dispersed in such a manner that the concentration of the fibers in at least one peripheral region is low enough, or is zero, so that the inner portion of said needle can be observed from outside.

12. The fiber-reinforced medical resin needle of claim 1, wherein the hub portion attached to the needle is provided with a connecting member which enables the needle to be mounted onto a syringe.

* * * * *

UNITED STATES PATENT AND TRADEMARK OFFICE
CERTIFICATE OF CORRECTION

PATENT NO. : 5,637,399
DATED : June 10, 1997
INVENTOR(S) : Makoto YOSHIKAWA et al It is certified that error appears in the above-indentified patent and that said Letters Patent is hereby corrected as shown below:

In Column 7, line 26, delete "Tothen" and insert -- Tohnen --.

Signed and Sealed this

Twenty-third Day of September, 1997

Attest:

BRUCE LEHMAN

Attesting Officer

Commissioner of Patents and Trademarks